(12) United States Patent
Caudill et al.

(10) Patent No.: US 7,151,178 B2
(45) Date of Patent: Dec. 19, 2006

(54) METHOD FOR THE PREPARATION OF 5-METHYLPYRAZINE-2-CARBOXYLIC ACID-4-OXIDE AND ITS SALTS

(75) Inventors: Jonathan Caudill, Ashville, OH (US); Mark Cooney, Grove City, OH (US); Satish C. Nigam, Hilliard, OH (US)

(73) Assignee: ISP Investments Inc., Wilmington, DE (US)

( * ) Notice: Subject to any disclaimer, the term of this patent is extended or adjusted under 35 U.S.C. 154(b) by 302 days.

(21) Appl. No.: 10/829,886

(22) Filed: Apr. 22, 2004

(65) Prior Publication Data

US 2005/0239803 A1    Oct. 27, 2005

(51) Int. Cl.
    *C07D 241/02* (2006.01)
(52) U.S. Cl. .................................................. 544/406
(58) Field of Classification Search .................. None
    See application file for complete search history.

(56) References Cited

U.S. PATENT DOCUMENTS

| 4,002,750 A | 1/1977 | Ambrogi et al. ............ 424/250 |
| 4,051,245 A | 9/1977 | Ambrogi et al. ............ 424/250 |
| 4,866,178 A | 9/1989 | Venturello et al. .......... 544/406 |

FOREIGN PATENT DOCUMENTS

| EP | 0201934 | 11/1986 |
| JP | 62-263164 | 11/1987 |

OTHER PUBLICATIONS

Mckay et al, "Oxidation Methods for Aromatic Diazines: Substituted Pyrazine-N-oxides, Pyrazine-N,N'dioxides, and 2,2':6',2"-terpyridine-1,1"-dioxide" Heterocyclic Communications, vol. 7(4), pp. 307-312 (2001). As Abstracted by CAS Online ("CAPLUS").*

Ambrogi et al, "Antilipolytic Activity of a Series of Pyrazine-N-Oxides" European Journal of Medicinal Chemistry, vol. 15(2), pp. 157-163 (1980).*

McKay et al, "Oxidation Methods for Aromatic Diazines: Substituted Pyrazine-N-Oxides, Pyrazine -N,N-Dioxides, and 2,2':6',2"-Terpyridine-1,1"-Dioxide" Heterocyclic Communications, vol. 7(4), pp. 307-312 (2001).*

DuPont Oxone® monopersulfate compound—Technical Information.

* cited by examiner

*Primary Examiner*—Zachary C. Tucker
(74) *Attorney, Agent, or Firm*—William J. Davis; Imre Balogh

(57) ABSTRACT

Methods for the preparation of pharmaceutically acceptable salts of 5-methylpyrazine-carboxylic acid-4-oxide by using the oxidizing agent OXONE® for the N-oxidation of $C_{1-4}$ methylpyrazinecarboxylic acid esters. The pharmaceutically acceptable salts are then formed by the saponification of the esters followed by alcohol precipitation.

4 Claims, No Drawings

METHOD FOR THE PREPARATION OF 5-METHYLPYRAZINE-2-CARBOXYLIC ACID-4-OXIDE AND ITS SALTS

BACKGROUND OF THE INVENTION

1. Field of the Invention

This invention relates to a process for the manufacture of 5-methylpyrazine-2-carboxylic acid-4-oxide, its esters and conversion of the esters to pharmaceutically acceptable salts thereof.

2. Description of the Related Art

5-Methylpyrazinecarboxylic acid has been produced by several methods. Examplary methods include the following:

Patent Nos. JP62263164 and EP201934 disclose the preparation of 5-methylpyrazine-carboxylic acid using hydrogen peroxide and a tungstate or molybdate catalyst.

U.S. Pat. No. 4,051,245 discloses a process for the preparation of 5-methylpyrazine-carboxylic acid by the use of peracid oxidation of 5-methylpyrazinecarboxamide followed by basic hydrolysis of the amide oxide and pH adjustment.

The present invention is also partly directed to the preparation of 5-methylpyrazine-carboxylic acid-4-oxides that exhibit hypoglycemic and hypolipaemic activity. These products are used as such but can result in severe irritation of the gastrointestinal lining because of their low pH. The use of inorganic salts of these acids should alleviate this physiological side effect.

The present invention is also directed to the transformation of the 5-methylpyrazine-carboxylic acid-2-oxides to their inorganic salts.

SUMMARY OF THE INVENTION

In accordance with the present invention, ester ($C_{1-4}$) and salts of 5-methylpyrazine-carboxylic acid are prepared as shown hereunder

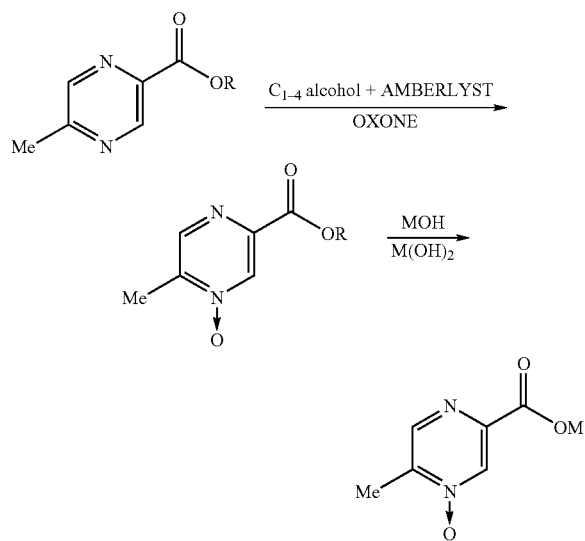

wherein:

R is a hydrogen atom or an alkyl group having from 1 to 4 carbon atoms; and

M is an inorganic salt of Na, K, Mg and Ca.

The $C_{1-4}$ esters of 5-methylpyrazinecarboxylic acid are prepared by heating the acid with the appropriate $C_{1-4}$ alcohol in the presence of a mineral acid such as sulfuric, hydrochloric, or acidic cation ion exchange resins (20–40 wt %). The ester is oxidized in a biphasic system consisting of a halogenated solvent and a 20–25% aqueous solution of peroxymonosulfate present as a component of a triple salt having the formula $2KHSO_5 \cdot KHSO_4 \cdot K_2SO_4$. Saponification of the isolated oxidation product results in formation of the desired salt, which is then precipitated with an alcohol. Alternatively, sodium or potassium salts are prepared by addition of sodium or potassium trimethylsilanolate to a solution of the oxidized ester in ether solvents such as diethyl ether or THF.

DETAILED DESCRIPTION OF THE INVENTION

The present invention relates to an improved scalable process for the manufacture of 5-methylpyrazinecarboxylic acid-4-oxide that exhibit hypoglycaemic and hypolipaemic activity. This product is used as such but can result in severe irritation of the gastrointestinal lining because of its low pH.; The use of inorganic (Na, K, Mg and Ca) salts of the acid should alleviate this physiological difficulty. This invention relates to a novel way of accomplishing the transformation to these pharmaceutically acceptable salts. Preparation of the N-oxide uses a safe, and easily handled oxidizing agent that allows the reaction to be carried out in the absence of metal peroxides or peracids at lower temperatures and in good yield.

In the process of the present invention the following reagents are used: acidic cation ion exchange resin as the catalyst, and peroxymonosulfate, $KHSO_5$, present as a component of a triple salt having the formula $2KHSO_5 \cdot KHSO_4 \cdot K_2SO_4$ an oxidizing agent which is a mixture of peroxymonosulfuric acid, monopotassium salt, dipotassium sulfate and potassium hydrogen sulfate which is an inexpensive, versatile, and relatively stable oxidizing agent that has been used to oxidize a number of functional groups including alkenes, arenes, amines, imines, and sulfides. OXONE® is also used for the preparation of dioxiranes. It has been used for the oxidation of several nucleic acids as well as nucleotides. It serves as a stoichiometric reagent under a variety of conditions (homogeneous and biphasic systems).

OXONE® is sold by Dupont and is used in denture cleansers, swimming pool/spa oxidizers, disinfectants, laundry bleaches and the like. Its active ingredient is potassium peroxymonosulfate, $KHSO_5$, which is present as a component of a triple salt having the formula $2KHSO_5 \cdot KHSO_4 \cdot K_2SO_4$.

In accordance with the invention and unlike other methods described in prior art, the reaction is carried out in a biphasic system that consists of a halogenated solvent typically, but not limited to, methylene chloride and a 20–25% aqueous solution of peroxymonosulfate $KHSO_5$ present as a component of a triple salt having the formula $2KHSO_5 \cdot KHSO_4 \cdot K_2SO_4$. The reaction mixture is vigorously stirred at room temperature, or preferably at reflux (40° C.), until the reaction is complete (analyzed by GC or GC/MS). The layers are separated and the aqueous layer is extracted with solvent. The combined extracts are dried with a drying agent, typically sodium or magnesium sulfate, and concentrated under reduced pressure. The isolated ester oxide is dried under vacuum. The dried material is then saponified, typically with sodium hydroxide, at 50° C. The product is precipitated by the addition of a pharmaceutically acceptable alcohol such as ethanol, isopropanol, or an appropriate specifically denatured alcohol (SDA). The salt is collected by filtration, washed with alcohol and dried under vacuum. The following further illustrates the process that is described in detail in conjunction with the non-limiting examples.

EXAMPLE 1

The reaction is carried out, under nitrogen, in a 1 L×4 neck flask equipped with a mechanical stirrer, water condenser (with gas inlet), and a thermocouple. The reactor is charged with 5-methylpyrazinecarboxylic acid (100 g), acidic cation ion exchange resin (20 g), and methanol (300 g). The mixture is stirred at reflux for about 20 h. After the reaction is complete (analyze with GC or GC/MS), the resin is removed by pressure filtration. The resin is rinsed with methanol. About 75% of the solvent is removed under reduced pressure and the resulting suspension is allowed to stand at room temperature overnight, and then in an ice bath for 3 h. The solid is collected by filtration and washed with ice-cold methanol (2×80 g). Drying under vacuum (25 inches of Hg) yielded 102.4 g (93%) of 5-methyl-2-pyrazonecarboxylic acid, methyl ester that is suitable for use as is.

EXAMPLE 2

The reaction is carried out, under nitrogen, in a 1 L×4 neck flask equipped with a mechanical stirrer, water condenser (with gas inlet), and a thermocouple. The reactor is charged with 5-methylpyrazinecarboxylic acid (100 g), ethanol ,(300 g) and sulfuric acid (2 g). The contents are refluxed for eight hours at 78° C. The reaction mixture is cooled to ambient temperature and sodium bicarbonate (4 g) is added. About 75% of the solvent is removed under reduced pressure and the resulting suspension is allowed to stand overnight. The solids are filtered and washed with cold methanol (2×80 g). Drying under oven (25 inches of Hg) yielded 101.25 g (84%) of 5-methyl-2-pyrazonecarboxylic acid, ethyl ester.

EXAMPLE 3

The reaction is carried out, under nitrogen, in a 1 L×4 neck flask equipped with a mechanical stirrer, water condenser (with gas inlet), and a thermocouple. The reactor is charged with 5-methylpyrazinecarboxylic acid, methyl ester (20.00 g), and methylene chloride (90 g). A solution of peroxymonosulfate, $KHSO_5$, present as a component of a triple salt having the formula $2KHSO_5.KHSO_4.K_2SO_4$ (84.67 g) in water (335 g) is added, and the mixture is vigorously stirred for 68 h at room temperature. The layers are separated, the organic layer is dried over magnesium sulfate, and gravity filtered. The aqueous layer is extracted with methylene chloride (3×135 g). Each extract is poured through the filter containing the magnesium sulfate from above. The extracts are combined and the solvent is removed by distillation at 55° C. Residual solvent is removed under vacuum (25 inches of Hg at 55°° C.) yielding 15.39 g (70%) of the n-oxide as an off-white solid).

EXAMPLE 4

The reaction is carried out, under nitrogen, in a 1 L×4 neck flask equipped with a mechanical stirrer, water condenser (with gas inlet), and a thermocouple. The reactor is charged with 5-methylpyrazinecarboxylic acid, propyl ester (21.69 g), and methylene chloride (80 g). A solution of peroxymonosulfate, $KHSO_5$, present as a component of a triple salt having the formula $2KHSO_5.KHSO_4.K_2SO_4$ (77.51 g) in water (305 g) is added, and the mixture is vigorously stirred for 46 h at 40° C. Analysis by GC indicated that the reaction is complete. The reaction mixture is transferred to a separatory funnel and the reactor is rinsed with methylene chloride (65 g). The solvent rinse is added to the separatory funnel. The layers are separated, and the organic, layer is dried over magnesium sulfate followed by pressure filtration. The aqueous layer is extracted with methylene chloride (3×120 g). Each extract is passed through the filter containing the magnesium sulfate from above. The extracts are combined and the solvent is removed by distillation at 55° C. Residual solvent is removed under vacuum (25 inches of Hg at 55° C.) yielding 17.94 g (75%) of the N-oxide as an off-white solid.

EXAMPLE 5

The reaction is carried out, under-nitrogen, in a 500 mL×4 neck flask equipped with a mechanical stirrer water condenser (with gas inlet), and a thermocouple. The reactor is charged with 5-methylpyrazinecarboxylic acid-4-oxide, methyl ester 15.00 g), and water (45 g). A solution of sodium hydroxide (3.93 g) in water (11 g) is added over 20 minutes at $\leq 12°$ C., and the mixture is stirred for 30 min at 50° C. The reaction mixture is cooled to <30° C. and aqueous HCl (0.90 g) is added bringing the pH from about 13 down to about 9. Isopropyl alcohol (80 g) is added to the reaction mixture over about 1 h at room temperature to precipitate the salt followed by overnight stirring. After stirring the suspension in an ice-bath for 3.5 h, the solid is collected and rinsed with ice-cold isopropyl alcohol (2×30 g). The collected solid is dried under vacuum (25 inches of Hg at 60° C.) to yield 12.53 g (80%) of the sodium salt as a off-white solid.

EXAMPLE 6

The reaction is carried out, under nitrogen, in a 500 mL×4 neck flask equipped with a mechanical stirrer, water condenser (with gas inlet), and a thermocouple. The reactor is charged with sodium trimethylsilanolate (3.71 g) and THF (90 g) 5-methylpyrazinecarboxylic acid-4-oxide, ethyl ester (6.00 g), is added and the mixture is stirred for 4 h at room temperature. The solid is collected and rinsed with THF (3×45 g). Drying under vacuum (25 inches of Hg at 65° C.) yielded 5.59 g (96%) of the sodium salt as an off-white solid.

It will be understood that changes and modification may be made to the present invention which are within the skill of the art. Such changes and modifications are intended to be covered limited only by the scope of the appended claims.

What is claimed is:

1. A method for the preparation of a 5-methylpyrazinecarboxylic acid ester-4-oxide comprising:
    reacting 5-methylpyrazinecarboxylic acid with a $C_{1-4}$ alcohol in the presence of an acidic cation exchange resin to obtain the ester of 5-methylpyrazine-carboxylic acid; and
    oxidizing the 5-methylpyrazinecarboxylic ester in the presence of potassium monopersulfate present as a component of a triple salt having the formula $2KHSO_5.KHSO_4.K_2SO_4$ in a halogenated solvent to obtain the isolated ester oxide.

2. A method for the preparation of the pharmaceutically acceptable inorganic salts of 5-methylpyrazinecarboxylic acid-4-oxide comprising oxidizing an ester of 5-methylpyrazine-carboxylic acid-4-oxide in a biphasic system consisting of a halogenated solvent and an aqueous solution of peroxymonosulfate present as a component of a triple salt having the formula $2KHSO_5 \cdot KHSO_4 \cdot K_2SO_4$ and saponifying said oxidized ester with an aqueous alkali or alkaline earth hydroxide to obtain the sodium or potassium salts of 5-methylpyrazine-carboxylic acid-4-oxide.

3. A method for the preparation of a pharmaceutically acceptable inorganic salt of a 5-methylpyrazinecarboxylic acid-4-oxide having the formula I

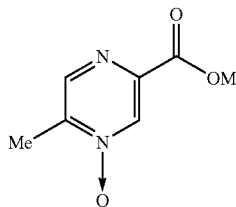

(I)

wherein

M is a cation of a metal selected from the group consisting of Na, K, Mg and Ca, comprising the steps of:

reacting 5-methylpyrazinecarboxylic acid or esters thereof, having the formula II

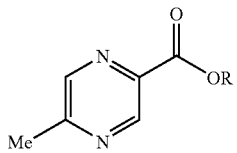

II wherein

R is H or an alkyl group having from 1 to 4 carbon atoms, with a $C_{1-4}$ alcohol in the presence of an acidic cation exchange resin to obtain an ester of the formula III

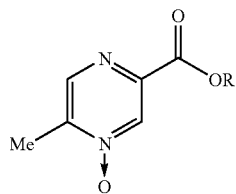

III wherein

R is H or $C_{1-4}$ alkyl;

oxidizing the ester of formula III in a biphasic system consisting of a halogenated solvent and an aqueous solution of peroxymonosulfate present as a component of a triple salt having the formula $2KHSO_5 \cdot KHSO_4 \cdot K_2SO_4$ to obtain an oxidation product; and saponificating the oxidation product to obtain the salt of formula I.

4. A method for the preparation of a pharmaceutically acceptable inorganic salt of a 5-methylpyrazinecarboxylic acid-4-oxide having the formula I

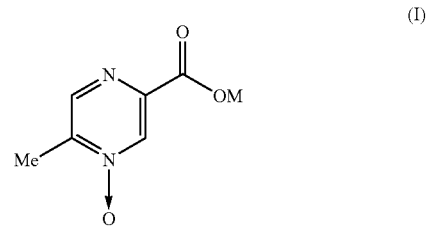

(I)

wherein:

M is selected from the group consisting of cations of alkali or alkaline earth metals selected from the group consisting of Na, K, Mg and Ca, comprising the steps of:

heating 5-methylpyrazinecarboxylic acid in a halogenated solvent in the presence of 20 to 40% w/w mineral acid selected from the group consisting of sulfuric acid and hydrochloric acid or an acidic cation exchange resin, and 20 to 25% w/w of an aqueous solution of peroxymonosulfate, KHSO5, present as a component of a triple salt having the formula $2KHSO_5 \cdot KHSO_4 \cdot K_2SO_4$ to obtain a solution;

stirring the solution until the reaction is complete;

separating the aqueous layer and extracting it with a solvent to obtain the ester oxide of 5-methylpyrazinecarboxylic acid;

drying said ester oxide;

saponifying said ester oxide;

precipitating a salt of said ester oxide by the addition of a pharmaceutically acceptable alcohol selected from the group consisting of ethanol, isopropanol and denatured alcohol;

collecting said salt by filtration;

washing said salt with alcohol; and drying said salt under vacuum.

* * * * *